United States Patent [19]

Hörig et al.

[11] Patent Number: 4,501,733
[45] Date of Patent: Feb. 26, 1985

[54] POLYPEPTIDES, A PROCESS FOR THEIR PREPARATION, THEIR USE, AND A PROCESS FOR THE PURIFICATION OF POLYPEPTIDES

[75] Inventors: Joachim Hörig, Stein; Hartmut Schultheiss, Raisdorf, both of Fed. Rep. of Germany

[73] Assignee: Ferring Arzneimittel GmbH, Kiel, Fed. Rep. of Germany

[21] Appl. No.: 467,187

[22] Filed: Feb. 16, 1983

[30] Foreign Application Priority Data

Feb. 19, 1982 [DE] Fed. Rep. of Germany ....... 3205991

[51] Int. Cl.³ .................... A61K 37/00; C07C 103/52
[52] U.S. Cl. .............................. 514/17; 260/112.5 R
[58] Field of Search .................. 260/112.5 R; 424/177

[56] References Cited

U.S. PATENT DOCUMENTS

| | | | |
|---|---|---|---|
| 4,223,019 | 9/1980 | Momany | 260/112.5 R |
| 4,223,020 | 9/1980 | Momany | 260/112.5 R |
| 4,223,021 | 9/1980 | Momany | 260/112.5 R |
| 4,224,316 | 9/1980 | Momany | 260/112.5 R |

OTHER PUBLICATIONS

European Journal of Pharmacology, vol. 77, Nr. 2-3, 1982, pp. 205-206, "Antagonists of Substance P, Stephanos Caranikas et al.

Chemical Abstracts, vol. 96, 1982, No. 96:116267d.

*Primary Examiner*—Delbert R. Phillips
*Attorney, Agent, or Firm*—Schwartz, Jeffery, Schwaab, Mack, Blumenthal & Koch

[57] ABSTRACT

Polypeptides of the formula I

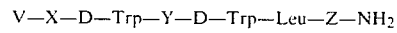

V—X—D—Trp—Y—D—Trp—Leu—Z—NH₂ wherein V represents a naturally occurring aminoacid or a physiologically acceptable acid radical, X represents a naturally occurring aminoacid or a single bond, Y represents one of the aminoacids, Phe, Ile, Val, Tyr and L—p—Cl—Phe, and Z represents the aminoacids Met or Nle, and salts thereof, in particular pharmaceutically acceptable salts thereof, a process for the preparation of these polypeptides and pharmaceutical products which contain these compounds. The invention also relates to a process for the purification of polypeptides by column chromatography.

5 Claims, 1 Drawing Figure

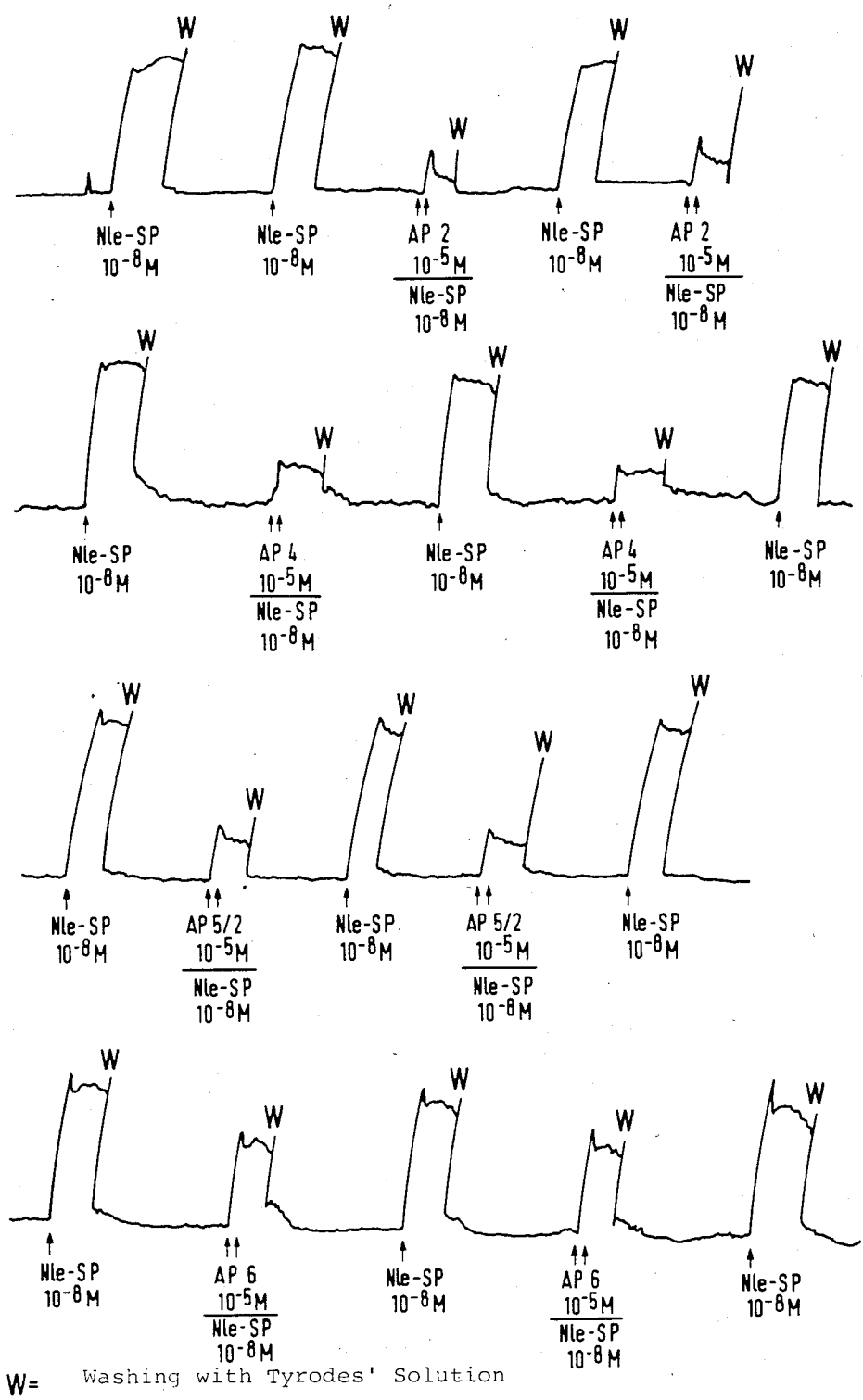

POLYPEPTIDES, A PROCESS FOR THEIR PREPARATION, THEIR USE, AND A PROCESS FOR THE PURIFICATION OF POLYPEPTIDES

BACKGROUND OF THE INVENTION

The present invention relates to new polypeptides which have pronounced antagonistic properties towards substance P, a process for their preparation, their use in combating diseases, and pharmaceutical products containing them. The invention furthermore relates to an advantageous process for the purification of polypeptides.

Euler and Gaddum ((1931), J. Physiol. (London) 72 74–87) were the first to describe a biological activity from tissue extracts which had a contraction-stimulating action on the jejunum of guinea pigs and a dilating action on the blood vessels in rabbits. They called the activity "substance P", but needless to say were not able to isolate the compound responsible in a pure form. This was only achieved later, when Leeman and Hammerschlag 1967 (Endocrinology 81, 803–810) discovered the salivant action of a hypothalamus fraction. As a result of this simple detection system, the study group was able to obtain the active principle in a homogeneous form (Chang & Leeman 1979, J. Biol. Chem. 245, 4784–4790). It was a peptide of the following structure:

Arg-Pro-Lys-Pro-Gln-Gln-Phe-Phe-Gly-Leu-Met-NH$_2$

This peptide was soon identified as substance P, since it had the same properties as the fractions partly purified by Euler and Gaddum. As the peptide was now accessible by synthesis (the first synthesis was described by Tregear et al. (1974, Nature (London) 232, 87–89), it was also possible to develop a specific radioimmunoassay for the peptide. This enabled the distribution of the substance in various tissues to be determined, and thus considerably stimulated research into substance P.

Substance P was detected in a large number of different tissues and cellular structures. Since this detection in most cases was by radioimmunological methods, the literature refers to ISP (immunoreactive substance P). Organs in which ISP occurs are: mammalian intestine, salivary gland, trachea, pancreas, kidney, bladder, prostate gland, substantia nigra, hypothalamus, pineal gland and dorsal horn.

ISP is evidently localized in nerves belonging to the autonomic nervous system and primary sensory nerve fibers (for example fibers responsible for referring pain). ISP has been found in the plexus myentericus (Auerbach's plexus) and in diffuse nerve fibers between the smooth muscle cells of the small intestine. ISP also occurs in endocrinal cells in the mucous membrane of the intestine.

An inhibitor which specifically blocks the action of the peptide would be of great advantage in the research into the biological functions of substance P.

Recently, specific and competitive inhibitors have been successfully synthesized. These are substances in which the aminoacids in positions 2, 7 and 9 are replaced by other aminoacids. D-Pro$^2$, D-Phe$^7$ and D-Trp-$^9$-SP (Folkers et al. (1981) Acta Physiol. Scand. 111, 505–506; and Rosell et al. (1981) Acta Physiol. Scand. 111, 381–382) inhibit the contraction of the ileum in guinea pigs caused by SP, SP-induced salivation and vasodilation caused by antidromic nerve stimulation and SP-induced vasodilation.

SUMMARY OF THE INVENTION

The object of the present invention is to discover new polypeptides which have a virtually exclusive antagonistic action towards substance P and are suitable as medicaments for humans and animals for combating certain diseases. The object of the invention is moreover to purify polypeptides in a simple and outstanding manner, so that they can be used without problems for the intended purpose mentioned.

The present invention accordingly relates to polypeptides of the formula

V-X-D-Trp-Y-D-Trp-Leu-Z-NH$_2$      (I)

wherein V represents a naturally occurring aminoacid or a physiologically acceptable acid radical, X represents a naturally occurring aminoacid or a single bond, Y represents one of the aminoacids Phe, Ile, Val, Tyr or L-p-Cl-Phe, and Z represents the aminoacids Met or Nle, and salts thereof.

DETAILED DESCRIPTION OF PREFERRED EMBODIMENTS

The process for the preparation of the polypeptides mentioned is characterized in that, in a manner which is known per se, by the solid phase method, first the C-terminal aminoacid and then the other aminoacids and the physiologically acceptable acid which the symbol V can represent, inter alia, are coupled to a carrier resin and the carrier resin is split off. The solid phase method is described in detail by Merrifield in (R. B. Merrifield (1963), J. Amer. Chem. Soc. 85, 2149–2154). The chloromethylated polystyrene (1% crosslinked) described therein is advantageously used as the solid phase.

In the solid phase synthesis of peptides, the C-terminal aminoacid is generally first covalently bonded to the resin. This is advantageously effected by reacting the Cs salts of the Boc-aminoacids with the chloromethyl groups of the resin. The resin and peptide are linked by an ester bond, CsCl being eliminated. Apart from the carboxyl group, the aminoacid should carry no other groups which are reactive during the coupling. The t-butoxycarbonyl group (Boc), for example, can be used for blocking the α-NH$_2$ group. The entire peptide is then built up stepwise on the first C-terminal aminoacid coupled with the resin.

The t-butoxycarbonyl group (Boc) can be introduced into aminoacids such as Pro, Gly, Phe, Ile, Leu, Nle, Met and D-trp with the aid of 2-(t-butoxycarbonyloxyimino)-2-phenylacetonitrile (Boc-ON) (M. Itoh, D. Hagiwara, T. Kamiya (1975), Tetrahedron Letters 4,393).

D-Trp (For) can be prepared, for example, by the method of M. Ohno, S. Tsukamoto, S. Makisuma and N. Izumiyu (1972) Bull. Chem. Soc. Jap. 45, 2852. Boc-Arg (HCl).H$_2$O can be prepared, for example, by the method of Kamushiro, Blake and Li (1972) J. Amer. Chem. Soc. 94, 2855.

After the first aminoacid has been introduced, the temporary protective group must be split off. This can be effected, for example, by acidolysis with trifluoroacetic acid-methylene chloride. In order to trap the t-butyl cations which are formed during the reaction and can undergo side reactions with the nucleophilic centers of the growing peptide chain, 10% by volume of anisole is advantageously also added to the reaction mixture.

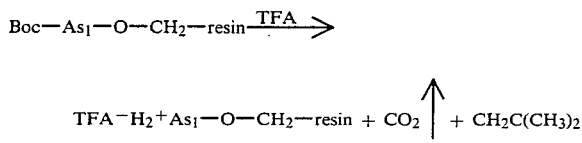

If the bonded aminoacid is in the form of a salt after the protective group has been split off, the ammonium group must first be converted into the free amine group to enable the next coupling to take place. In the preferred embodiment described above, the bonded aminoacid is in the form of its trifluoroacetyl salt after the Boc protective group has been split off by trifluoroacetic acid. To enable the next coupling to take place, the ammonium group must be converted into the free amine form. This is effected with triethylamine.

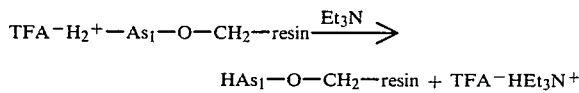

The coupling to the second aminoacid can then be carried out.

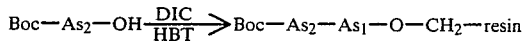

The reaction sequence: splitting off of the Boc protective group—liberation of the amino group from its salt bonding—coupling with the next Boc-aminoacid is continued until all the aminoacids have been coupled to the resin.

After the Boc-protected aminoacid has been coupled with the free amino groups of the resin or the peptide chain, the ninhydrin test according to Kaiser (Kaiser, E., Coloscott, R. L., Bossinger, C. C. and Cook, P. L. (1970) Anal. Biochem. 34 (595–598) is used on a small sample of resin to investigate whether free amino groups can still be detected (blue coloration). If this is the case, the resin must be subjected to renewed coupling, in order to prevent the formation of peptides lacking one aminoacid, or to acetylation. During the final purification, it would be possible to separate off these peptides from the actual product only with great difficulty.

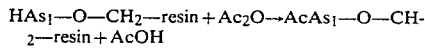

In the above general formula I, the symbol V preferably represents the aminoacids Arg, Lys, Orn or Pro. The symbol X preferably represents the aminoacid Gln.

If the symbol V represents a physiologically acceptable acid radical, this is advantageously the radical of a lower aliphatic carboxylic acid with 1 to 6 carbon atoms, preferably acetic acid and particularly preferably propionic acid.

The last 5 aminoacids as defined in formula I are essential in the polypeptides of the formula I according to the invention. In contrast, it is of no consequence which aminoacids the symbols V and X represent. If V and X denote aminoacids, the compounds are heptapeptides. If X represents a single bond, the compounds are hexapeptides. The pharmacological action of the compounds according to the invention is thus largely independent of which aminoacids the symbols V and/or X represent. Since the compounds according to the invention advantageously have a certain solubility in water, so that they can advantageously be used pharmacologically, the aminoacids represented by the symbols V and X should not both be highly non-polar. The abovementioned preferred aminoacids represented by these symbols are preferred from this point of view. The expert can easily use other aminoacids which likewise have a certain polarity and result in the polypeptides according to the invention having a sufficient solubility in water. Because they are more easily accessible, naturally occurring aminoacids are employed according to the invention. In principle, however, it is also possible to use aminoacids which are only accessible by synthesis.

The invention thus also relates to the use of the polypeptides mentioned or of their pharmaceutically acceptable salts in combating pain conditions and hypertension diseases, especially chronic cases thereof. These indications also include, for example, chronic inflammation of the cornea of the eye, which can be caused by various circumstances, for example by continual exposure to UV light, IR radiation or chemical compounds.

The invention furthermore relates to pharmaceutical products which contain one or more of the above-mentioned peptides or their pharmaceutically acceptable salts, together with the conventional pharmaceutical excipients and/or auxiliaries.

The polypeptides according to the invention possess an exceptionally pronounced antagonistic property without a noticeable agonistic action towards substance P.

The abbreviations used in the description have the following meanings:

| Abbreviations | |
| --- | --- |
| 1-HBT | 1-hydroxybenzotriazole |
| DIC | diisopropylcarbodiimide |
| TFA | trifluoroacetic acid |
| Et$_3$N | triethylamine |
| Boc | t-butoxycarbonyl |
| For | formyl |
| DMF | dimethylformamide |
| MeOH | methanol |
| Nle | norleucine |
| Met | methionine |
| Leu | leucine |
| Trp | tryptophan |
| Phe | phenylalanine |
| Gln | glutamine |
| Pro | proline |
| Arg | arginine |
| Tyr | tyrosine |
| Ile | isoleucine |
| Val | valine |
| L-p-Cl—Phe | p-chlorophenylalanine |
| Lys | lysine |
| Orn | ornithine |

The invention moreover relates to a process for the purification of polypeptides by column chromatography, which is characterized in that the solution of the polypeptide is adsorbed onto a polystyrene ion exchanger resin and is eluted with water/acetonitrile/acetic acid mixtures with an increasing content of acetonitrile. The appropriate commercially available resins can be used as the polystyrene ion exchanger resins, such as, inter alia, those mentioned in the examples. The adsorption is carried out with a solution of the polypeptide, advantageously in aqueous acetic acid, the content of acetic acid advantageously being about 20 to 80% by weight, preferably 40 to 60 and particularly preferably about 50% by weight. Before the adsorption, the column of exchanger resin is advantageously equilibrated with acetic acid, the concentration of which in this case is advantageously in the range from about 2 to 40% by weight, preferably 2 to 20 and particularly preferably 4 to 8% by weight. The column is then eluted with water-/acetonitrile/acetic acid mixtures, the elution first advantageously being only with aqueous acetic acid. The column is then eluted with water/acetonitrile/acetic acid mixtures with an increasing acetonitrile content. The amount of acetic acid and, where relevant, acetonitrile in these aqueous mixtures is advantageously 2 to 20% by weight, preferably about 4 to 8% by weight. The elution can be gradual or continuous. The content of acetonitrile is increased stepwise in the case of gradual elution and continuously in the case of continuous elution. The particular advantageous ratios between the acetonitrile and acetic acid can be determined, in each case according to the amino-acid to be purified, by simple experiments.

The invention is illustrated in more detail with the aid of the examples which follow.

The aminoacids employed and the aminoacids shown by the abbreviations in the formula are in each case in the L-configuration, unless indicated otherwise.

EXAMPLE 1

(A) Coupling of the first aminoacid to the resin (F. Gisin (1973) Helv. Chim. Acta 56, 1976).

2,5 g of Boc-Met-OH and 1.63 g of $Cs_2CO_3$ were dissolved in 25 ml of $H_2O$. The solution was concentrated to dryness and the residue was dried in vacuo. The residue was dissolved in 30 ml of DMF, 5 g of chloromethylated polystyrene resin (1% crosslinked, 1 meq. of Cl/g of resin) were added and the mixture was stirred at room temperature for 4 days. The solvent was then filtered off and the resin was washed with 3 50 ml portions of DMF, 2 50 ml portions of MeOH, 2 50 ml portions of DMF, 1 50 ml portion of MeOH and 2 50 ml portions of diethyl ether.

After drying, 5.83 g of Boc-Met-O-$CH_2$-resin were obtained. The degree of substitution was 77%. An analogous procedure was followed in order to couple Boc-Nle-OH to the resin.

The individual steps which were carried out with the resin in one and the same manual peptide synthesis apparatus are described in detail in the text which follows. The amounts for 5 g of resin are given.

| Solvent/reagent | Volume (ml) | Stirring time (minutes) | Operation |
| --- | --- | --- | --- |
| (a) Neutralization | | | |
| $CH_2Cl_2$ | 40 | 3 | washing |
| $CH_2Cl_2/Et_3N = 9/1$ | 50 | 5 | neutralization |
| $CH_2Cl_2$ | 40 | 3 | washing |
| (b) Coupling of the aminoacid | | | |
| $CH_2Cl_2$ | 40 | 3 | washing |
| 15 mmoles of Boc—aminoacid + 15 mmoles of 1-HBT + 15 mmoles of DIC in 40 ml of DMF | 40 | 180 | coupling |
| DMF (repeated 3 times) | 40 | 3 | washing |
| $CH_2Cl_2$ (repeated 3 times) | 40 | 3 | washing |
| 2-PrOH (repeated 3 times) | 40 | 3 | washing |
| $CH_2Cl_2$ | 40 | 3 | washing |
| (c) Splitting off of the Boc protective group | | | |
| $CH_2Cl_2$ | 40 | 3 | washing |
| $TFA/CH_2Cl_2$/anisole = 45/45/10 | 40 | 1.5 | deprotection |
| $TFA/CH_2Cl_2$/anisole = 45/45/10 | 40 | 1.5 | deprotection |
| $TFA/CH_2Cl_2$/anisole = 45/45/10 | 40 | 15 | deprotection |
| $CH_2Cl_2$ (repeated 3 times) | 40 | 3 | washing |
| 2-PrOH (repeated 3 times) | 40 | 3 | washing |
| $CH_2Cl_2$ (repeated 3 times) | 40 | 3 | washing |
| (d) Acetylation of the resin | | | |
| $CH_2Cl_2$ | 40 | 3 | washing |
| $CH_2Cl_2/Ac_2O$/pyridine = 80/10/10 | 50 | 3 | coupling |
| $CH_2Cl_2/Ac_2O$/pyridine = 80/10/10 | 50 | 20 | coupling |
| $CH_2Cl_2$ (repeated 3 times) | 40 | 3 | washing |
| 2-PrOH (repeated 3 times) | 40 | 3 | washing |
| $CH_2Cl_2$ (repeated 3 times) | 40 | 3 | washing |

(B) Synthesis of the peptide resin Arg-Gln-D-Trp-Phe-D-Trp-Leu-Met-$NH_2$ (a) Synthesis of this peptide was achieved by carrying out the reaction steps described in the preceding section one after the other in the reaction sequence shown in the table which follows. The synthesis was started with 5 g of polychloromethylated resin with 0.77 meq. of Boc-Met/g of resin:

| Reaction step | Compound | Reaction sequence |
| --- | --- | --- |
| 1 | Boc—Leu—Met—O—resin | c-a-b-d |
| 2 | Boc—D-Trp—Leu—Met—O—resin | c-a-b-d |
| 3 | Boc—Phe—D-Trp—Leu—Met—O—resin | c-a-b-d |
| 4 | Boc—D-Trp—Phe—D-Trp—Leu—Met—O—resin | c-a-b-d |
| 5 | Boc—Gln—D-Trp—Phe—D-Trp—Leu—Met—O—resin | c-a-b-d |
| | 1.68 g of this resin (8.4 g in total) were further processed | |
| 6 | Boc—Arg—Gln—D-Trp—Phe—D-Trp—Leu—Met—O—resin | c-a-b |

(b) Ammonolysis and deprotection 2.0 g of Boc-Arg(HCl)-Gln-D-Trp-Phe-D-Trp-Leu-Met-O-resin were suspended in 15 ml of methanol, which was saturated with ammonia. The mixture was stirred at room temperature for 48 hours and was then filtered and the filtrate was evaporated. The resulting oil was triturated with 50 ml of ethyl acetate and the mixture was left to stand overnight at 0°. The precipitate was filtered off (750 mg). This material was dissolved in a mixture of 10 ml of DMF, 5 ml of 10 N HCl and 5 ml of $H_2O$ and the solution was stirred at room temperature for 2 hours. The solution was evaporated and the residue was taken up in water/acetic acid and lyophilized.

(c) Column chromatography on Servachrom XAD-2 (registered trademark)

A column of Servachrom XAD-2, 100–120 mesh (24×2.5 cm) was equilibrated with 6% of AcOH. The substance (about 600 mg) was dissolved in 5 ml of 30% strength AcOH and the solution was discharged onto the column. The column was then chromatographed with a mixture of 470 ml of $H_2O$, 30 ml of AcOH and 88 ml of $CH_3CN$. The flow rate was 0.4 ml/minute, and the fraction size was 10 ml. The desired substance was eluted in fractions 51–105. These were collected and evaporated and the residue was lyophilized.

Yield: 160 mg (120 μmoles, 15% of theory, based on the Boc-Met content of the resin).

Analysis of H-Arg-Gln-D-Trp-Phe-D-Trp-Leu-Met-$NH_2$ High pressure liquid chromatography The substance showed a single symmetric peak in the following high pressure liquid chromatography system:
Column: μ-Bondapak C18
Eluant: $CH_3CN$/K-phosphate buffer pH 3.0, $0.1^M = 35/65$
Flow rate: 1.5 ml/minute
Retention time: 8.33 minutes
Thin layer chromatography:
The substance showed a single symmetric peak in the following mobile phase systems (carrier: silica gel 60): migration distance: 15 cm.

|  | $R_f$ |
|---|---|
| 2-PrOH/1 M AcOH = 2:1 | 0 |
| EtOAc/Py/AcOH/$H_2O$ = 60:20:6:11 | 0.115 |
| n-BuOH/AcOH/$H_2O$ = 4:1:1 | 0.401 |
| EtOAc/Py/AcOH/$H_2O$ = 120:20:6:11 | 0 |

Aminoacid analysis

About 1 mg of peptide was hydrolyzed in 1 ml of 6N HCl at 110° for 24 hours. The following results were obtained: Glu 1.03 (1), Met 1.0 (1), Leu 0.94 (1), Phe 0.97 (1), Arg 1.06 (1).

EXAMPLES 2 AND 3

H-Pro-Gln-D-Trp-Phe-D-Trp-Leu-Met-$NH_2$
Pr-Gln-D-Trp-Phe-D-Trp-Leu-Met-$NH_2$ (a) Synthesis of these peptides was achieved in carrying out the reaction steps described in more detail in example 1 one after the other in the reaction sequence shown in the table. The synthesis was started with 5.83 g of Boc-Met-O-resin (0.77 meq. of Boc-Met/g of resin).

| Reaction step | Compound | Reaction sequence |
|---|---|---|
| 1 | Boc—Leu—Met—O—resin | c-a-b |
| 2 | Boc—D-Trp(For)—Leu—Met—O—resin | c-a-b |
| 3 | Boc—Phe—D-Trp(For)—Leu—Met—O—resin | c-a-b |
| 4 | Boc—D-Trp(For)—Phe—D-Trp(For)—Leu—Met—O—resin | c-a-b |
| 5 | Boc—Gln—D-Trp(For)—Phe—D-Trp(For)—Leu—Met—O—resin In each case 2.18 g of this peptide resin (8.74 g) were used for synthesis of the two end products. | c-a-b |
| 6a | Boc—Pro—Gln—D-Trp(For)—Phe—D-Trp(For)—Leu—Met—O—resin | c-a-b |
| 7a | TFA.Pro—Gln—D-Trp(For)—Phe—D-Trp(For)—Leu—Met—O—resin | c |
| 6b | Pr—Gln—D-Trp(For)—Phe—D-Trp(For)—Leu—Met—O—resin | c-a-b |

(b) Ammonolysis of H-Pro-Gln-D-Trp(For)-Phe-D-Trp(For)-Leu-Met-O-$CH_2$-resin 20 ml of methanol, which had first been saturated with gaseous ammonia at 0°, was poured over 2.33 g of the resin and the mixture was stirred at room temperature in a well-sealed round-bottomed flask for 24 hours. The suspension was then filtered and the resin was washed with 5 50 ml portions of methanol. The dried resin then weighed 1.3 g. The clear filtrate was evaporated and the oily residue was dried in vacuo. Weight: 1.06 g.

(c) Purification of H-Pro-Gln-D-Trp-Phe-D-Trp-Leu-Met-$NH_2$ by column chromatography The product from (b) was discharged, as a solution in 10 ml of 50% strength AcOH, onto a column of Servachrom XAD-2 (100–120 mesh, 2.5×45 cm), which had first been equilibrated with 6% strength acetic acid. The column was eluted with the following eluants in succession:
1. 400 ml of 6% strength AcOH
2. 400 ml of 6% strength AcOH/$CH_3CN$ = 9:1
3. 400 ml of 6% strength AcOH/$CH_3CN$ = 8:2
4. 400 ml of 6% strength AcOH/$CH_3CN$ = 7:3
5. 800 ml of 6% strength AcOH/$CH_3CN$ = 6:4

The fraction size was 10 ml, and the flow rate was 10 ml/25 minutes. The product was eluted in fractions 251–271. The solution was evaporated and the residue was taken upon in n-BuOH/water and lyophilized.

(d) Analysis:

High pressure liquid chromatography: The product shows a single symmetric peak when chromatographed in the following system:
Column: μ-Bondapak $C_{18}$ (Messrs. Waters) (2.4×300 mm)
Eluant: $CH_3CN$ (40%)/0.1M K-phosphate buffer pH 3.0 (60%)

The retention time observed was 15.8 minutes (flow rate: 1.5 ml/minute).

Thin layer chromatography:

The substance showed a single symmetric spot in 4 different systems. Merck precoated silica gel 60 plates (5×20 cm) were used as the solid phase.

|  | $R_f$ |
|---|---|
| n-BuOH/AcOH/$H_2O$ = 4:1:1 | 0.64 |
| 2-PrOH/1 M AcOH = 2:1 | 0.191 |
| EtOAc/Py/AcOH/$H_2O$ = 60:20:6:11 | 0.51 |
| EtOAc/Py/AcOH/$H_2O$ = 120:20:6:11 | 0.19 |

Aminoacid analysis

The peptide (about 1 mg) was hydrolyzed in 1 ml at 4M methanesulfonic acid at 120° C. for 24 hours.

The following values were obtained: Glu 1.06 (1), Pro 1.07 (1), Met 0.94 (1), Leu 0.99 (1), Phe 0.92 (1), $NH_3$ 1.96 (2), Trp 2.05 (2).

(e) Ammonolysis of propionyl-Gln-D-Trp(For)-Phe-D-Trp(For)-Leu-Met-O-$CH_2$-resin 2.15 g of the resin was stirred with 20 ml of methanol, which had first been saturated with gaseous ammonia at 0°, for 24 hours in a well-sealed round-bottomed flask.

The suspension was then filtered and the resin was washed with 5 30 ml portions of methanol. The weight of the resin was then 1.22 g. The clear filtrate was evaporated and the oily residue was dried in vacuo.

Weight: 900 mg.

(f) Purification by column chromatography Propionyl-Gln-D-Trp-Phe-D-Trp-Leu-Met-NH$_2$ The product was dissolved in 10 ml of 50% strength AcOH and the solution was discharged onto a column of Servachrom XAD-2 (100–120 mesh, 2.5×45 cm) which had first been equilibrated with 6% strength acetic acid. The column was eluted with the following eluants in succession:

1. 400 ml of 6% strength AcOH
2. 400 ml of 6% strength AcOH/CH$_3$CN=9:1
3. 400 ml of 6% strength AcOH/CH$_3$CN=8:2
4. 400 ml of 6% strength AcOH/CH$_3$CN=7:3
5. 800 ml of 6% strength AcOH/CH$_3$CN=6:4

The flow rate was 10 ml/25 minutes, and the fraction size was 10 ml. The product was eluted in fractions 171–189. The solution was lyophilized. Yield: 93 mg (chromatographically pure product)+240 mg (chromatographically slightly contaminated).

(g) Analysis:

High pressure liquid chromatography: The analsis was carried out under the same conditions as described above. The substance showed a single symmetric peak with a retention time of 18 minutes. TLC (thin layer chromatography): The substance showed a single symmetric spot in four different mobile phase systems:

|  | $R_f$ |
|---|---|
| n-BuOH/AcOH/H$_2$O = 4:1:1 | 0.78 |
| n-PrOH/1 M AcOH = 2:1 | 0.55 |
| EtOAc/Py/AcOH/H$_2$O = 60:20:6:1 | 0.76 |
| EtOAc/Py/AcOH/H$_2$O = 120:20:6:1 | 0.4 |

Pharmacological investigations

Material and method

The ileum from guinea pigs was cut out after the animals had been sacrificed, was substantially freed from mesenteria by pulling at the caudal end and was freed from digestion products with Tyrode's solution. About 25 cm were discarded from the caudal end, and several sections of intestine 4 cm long were then removed and stored in Tyrode's solution. The Tyrode's solution was gassed with carbogen (95% of O$_2$ and 5% of CO$_2$). The Tyrode's solution contained the following substances per liter: 8 g of NaCl; 2 g of KCl; 1.3 g of CaCl$_2$.2H$_2$O; 2.1 g of MgCl$_2$.6H$_2$O; 10 g of NaHCO$_3$; 0.58 g of NaH$_2$PO$_4$.1H$_2$O; and 11 g of D(+)-glucose.

The Tyrode's solution was thermostatically controlled at 38° C. in an organ bath. Each preparation retained its complete contractility for 4 to 7 hours. 4 cm sections of intestine were tied on both sides and suspended in the organ bath. The contractions of the preparation were recorded under isotonic measurement conditions via a lever on a Kymograph drum. The writing was done by a felt-tip pen arranged as a lateral pen. The load arm was 225 mm and the power arm 20 mm long. The pre-load was about 0.3 g and the paper speed was 5 mm/minute. The organ bath contained 10 ml.

As a rule, the test substances were added in volumes of 2 to 100 μl, and were distributed instantaneously in the organ bath by the gassing. All the test substances added were dissolved in Tyrode's solution or diluted with Tyrode's solution from a stock solution.

Test substances: substance P (Serva) or norleucine-SP (Ferring, Kiel) were used as agonists, in doses of between $10^{-9}$ and $10^{-7}$M. The following compounds were tested as potential antagonists:

Compound 1(AP2): D-Pro$^2$, D-Trp$^{7,9}$-SP
Compound 2(AP4): Arg$^5$, D-Trp$^{7,9}$-SP$_{5-11}$
Compound 3(AP5/2): Pro$^5$, D-Trp$^{7,9}$-SP$_{5-11}$
Compound 4(AP6): Propionyl D-Trp$^{7,9}$-SP$_{6-11}$ In the standard test, SP or Nle-SP was applied in a concentration of between $10^{-9}$ and $10^{-7}$M, and was washed out after about 2 minutes. After a latency period of a further 3 minutes, the potential antagonist was applied in a concentration of $3\times10^{-6}$, $10^{-5}$ or $3.3\times10^{-5}$M, directly followed by a further dose of SP (Nle-SP). After renewed washing out and a waiting time of 3 minutes, SP (Nle-SP) was again applied in the same dose, in order to investigate whether the original contraction strength is reached.

The reduction in the relative contraction of the ileum preparations as a result of using SP analogs was regarded as a measure of the relative activity as antagonists.

Results

All the analogs of substance P tested: compounds 1, 2, 3 and 4, have a substance P-antagonizing action when they are used in a concentration of $10^{-5}$M. There is a dependency on the dose of the agonist (SP or Nle-SP). In the lower dose range, the antagonists have a more powerful action than in the upper range.

For comparison of the activity of the various antagonists, their inhibiting actions found when the agonist is in a concentration of $10^{-8}$M, and the antagonist is in a concentration of $10^{-5}$M are shown in the TABLE.

| Agonist | Antagonist | Percentage inhibiting action | Number of experiments |
|---|---|---|---|
| SP or | compound 1 (AP 2) $10^{-5}$ M | 67.0 ± 3 | 2 |
| Nle—SP | compound 2 (AP 4) $10^{-5}$ M | 68.1 ± 8 | 7 |
| $10^{-8}$ M | compound 3 (AP 5/2) $10^{-5}$ M | 69.5 ± 0.5 | 2 |
|  | compound 4 (AP 6) $10^{-5}$ M | 29.3 ± 9.5 | 3 |

According to the present findings, compounds 1, 2 and 3 have the most powerful action. They have approximately the same antagonistic potency.

In contrast, compound 4, which is a shorter peptide by one aminoacid, has a lower but significant inhibiting action.

Original records of the isotonic measurement data are to be found in FIG. 1.

We claim:

1. Polypeptides of the formula

V-X-D-Trp-Y-D-Trp-Leu-Z-NH$_2$ wherein V represents Arg, Lys, Orn or Pro, X represents Gln or a single bond, Y represents one of the aminoacids Phe, Ile, Val, Tyr or L-p-Cl-Phe, and Z represents the aminoacids Met or Nle, and salts thereof.

2. Polypeptides according to claim 1, wherein V represents Arg or Pro.

3. An analgesic, antiinflammatory antispasmodic or antiptyalistic pharmaceutical composition comprising:
   (a) a physiologically compatible drug carrier; and (b) a therapeutically effective concentration of a composition comprising a polypeptide of the formula V-X-D-Trp-Y-D-Trp-Leu-Z-NH$_2$ wherein V represents Arg, Lys, Orn or Pro, X represents Gln or a single bond, Y represents one of the aminoacids Phe, Ile, Val, Tyr or L-p-Cl-Phe, and Z represents the aminoacids Met or Nle, or a salt of said polypeptide.

4. A pharmaceutical composition according to claim 3, wherein said amount is sufficient to cause an antispasmodic effect.

5. A pharmaceutical composition according to claim 3, wherein V represents Arg or Pro.

* * * * *